United States Patent
Breviere et al.

(10) Patent No.: US 8,448,495 B2
(45) Date of Patent: May 28, 2013

(54) DEVICE FOR QUANTIFYING THE CONTENTS OF AT LEAST ONE GASEOUS CONSTITUENT CONTAINED IN A GASEOUS SAMPLE FROM A FLUID, RELATED ASSEMBLY AND PROCESS

(75) Inventors: Jérôme Breviere, Taverny (FR); Douglas Baer, Menlo Park, CA (US); Michael John Whiticar, Victoria (CA)

(73) Assignee: Geoservice Equipments, Roissy-en-France (FR)

(*) Notice: Subject to any disclaimer, the term of this patent is extended or adjusted under 35 U.S.C. 154(b) by 506 days.

(21) Appl. No.: 12/309,970

(22) PCT Filed: Aug. 10, 2007

(86) PCT No.: PCT/IB2007/002318
§ 371 (c)(1), (2), (4) Date: Sep. 2, 2009

(87) PCT Pub. No.: WO2009/037517
PCT Pub. Date: Mar. 26, 2009

(65) Prior Publication Data
US 2010/0162791 A1 Jul. 1, 2010

(30) Foreign Application Priority Data
Aug. 11, 2006 (EP) .................................... 06291305

(51) Int. Cl.
*G01N 21/72* (2006.01)
(52) U.S. Cl.
USPC ........... 73/31.05; 250/343; 436/155; 436/161
(58) Field of Classification Search
USPC ............ 73/23.2, 23.3, 23.31, 31.05; 250/255, 250/340, 341.1, 343, 344, 363.01; 436/155, 436/161
See application file for complete search history.

(56) References Cited

U.S. PATENT DOCUMENTS

| | | | | |
|---|---|---|---|---|
| 3,588,496 A | * | 6/1971 | Snowman | 50/343 |
| 3,904,500 A | * | 9/1975 | Jensen | 204/157.2 |
| 4,010,100 A | * | 3/1977 | Suslick | 95/82 |
| 4,064,025 A | * | 12/1977 | Chen | 204/157.22 |
| 4,366,379 A | * | 12/1982 | Cotter | 204/157.22 |
| 4,563,258 A | * | 1/1986 | Bridges | 204/157.22 |
| 4,690,742 A | * | 9/1987 | Cantrell et al. | 204/157.2 |
| 4,734,177 A | * | 3/1988 | Robinson et al. | 204/157.2 |
| RE33,493 E | * | 12/1990 | Lee et al. | 250/343 |
| 5,246,868 A | | 9/1993 | Busch et al. | |
| 5,317,156 A | * | 5/1994 | Cooper et al. | 250/345 |
| 5,445,964 A | * | 8/1995 | Lee et al. | 436/60 |
| 5,747,809 A | * | 5/1998 | Eckstrom | 250/345 |
| 5,827,405 A | * | 10/1998 | Averbukh | 204/157.2 |

(Continued)

Primary Examiner — David Rogers
(74) Attorney, Agent, or Firm — Wenderoth, Lind & Ponack, L.L.P.

(57) ABSTRACT

This device includes a stage for forming a gaseous flow from the sample, and a column for separation by selective retention of each gaseous constituent. It includes an oven for combustion of the gaseous flow in order to form a gaseous residue from each constituent, and a quantification unit for quantifying the content of each constituent to be analyzed in the gaseous flow. The quantification unit includes an optical measurement cell connected to an oven, and a mirror for introducing a laser incident optical signal into the cell. The quantification unit also measures a transmitted optical signal resulting from an interaction between the optical signal and each gaseous residue in the cell, and calculates the content on the basis of the transmitted optical signal.

17 Claims, 5 Drawing Sheets

U.S. PATENT DOCUMENTS

| | | | |
|---|---|---|---|
| 6,483,589 B1 * | 11/2002 | Suzuki et al. | 356/437 |
| 6,888,127 B2 * | 5/2005 | Jones et al. | 250/269.1 |
| 6,967,322 B2 * | 11/2005 | Jones et al. | 250/269.1 |
| 7,351,316 B2 * | 4/2008 | Yoshida et al. | 204/252 |
| 7,427,760 B2 * | 9/2008 | Weidmann | 250/343 |
| 7,520,158 B2 * | 4/2009 | DiFoggio | 73/19.1 |
| 7,994,479 B2 * | 8/2011 | Weidmann | 250/343 |
| 2003/0134427 A1 * | 7/2003 | Roller et al. | 436/171 |
| 2003/0160164 A1 * | 8/2003 | Jones et al. | 250/269.1 |
| 2005/0099618 A1 | 5/2005 | DiFoggio et al. | |
| 2006/0084180 A1 * | 4/2006 | Paldus et al. | 436/171 |
| 2007/0081162 A1 * | 4/2007 | Roller et al. | 356/437 |
| 2007/0178011 A1 * | 8/2007 | Elrod et al. | 422/78 |
| 2008/0147326 A1 * | 6/2008 | Ellis | 702/9 |
| 2010/0055802 A1 * | 3/2010 | Zare et al. | 436/158 |

* cited by examiner

DEVICE FOR QUANTIFYING THE CONTENTS OF AT LEAST ONE GASEOUS CONSTITUENT CONTAINED IN A GASEOUS SAMPLE FROM A FLUID, RELATED ASSEMBLY AND PROCESS

BACKGROUND OF THE INVENTION

The present invention relates to a device for quantifying the content of at least one gaseous constituent contained in a gaseous sample from a fluid. The device includes: a means for forming a gaseous flow from the sample, comprising means for separation by elective retention of each gaseous constituent to be analysed; a means for combustion of the gaseous flow, connected to the separation means in order to successively form a gaseous residue from each constituent; and a means for quantifying the content of each constituent to be analysed in the gaseous flow.

This device is used in particular to analyse the gases extracted from a petroleum fluid produced in an oil well or to determine the content of the hydrocarbon constituents contained in drilling mud.

In the last case, when an oil or other outflow well is drilled (in particular gas, vapor, water), it is known to carry out an analysis of the gaseous compounds contained in the drilling muds originating from the well. This analysis allows the geological sequence of the formations passed through during the drilling operation to be reconstructed, and is used to determine the possible applications of the fluid deposits encountered.

This analysis, which is carried out in a continuous manner, comprises two main phases. The first phase consists in extracting the gases carried by the mud (for example, hydrocarbon compounds, carbon dioxide, hydrogen sulphide). The second phase consists in qualifying and quantifying the extracted gases.

In order to extract the gases from the mud, a degassing means with mechanical agitation of the type described in FR 2 799 790 is often used. The gases extracted from the mud, mixed with a carrier gas which is introduced into the degassing means, are conveyed by means of suction through a gas extraction pipe to an analysis device which allows the extracted gases to be quantified.

The analysis device comprises a gas-phase chromatograph (GPC) which allows the various gases collected in the degassing means to be separated in order to be able to quantify them.

In some cases, however, it is necessary to carry out a more precise analysis of the gaseous content of the extracted gases, using a device for measuring the relationship between the contents of carbon isotopes $^{13}C$ and $^{12}C$ in the gaseous hydrocarbon compounds extracted from the mud.

A device of this type comprises, in conjunction with the gas-phase chromatography, a combustion oven and an isotope ratio mass spectrometer (IRMS) which is intended to analyze the outflow from the combustion oven.

A device of this type is unsatisfactory, in particular when the analysis must be carried out on a drilling site or on a production site. The IRMS must be kept under pressure and temperature conditions which are substantially constant in order to obtain precise and repetitive measurements. Consequently, it is necessary to carry out an "off-line" analysis of the samples in a climate-controlled laboratory. If it is desirable to carry out the analysis "on-line", however, it is necessary to bring a large, fragile and complex climate control and IRMS control assembly close to the well in an environment which can be hostile and inaccessible.

SUMMARY OF THE INVENTION

An object of the invention is therefore to provide a device for quantifying the content of at least one gaseous constituent from a fluid. The device can readily be arranged in the vicinity of an oil well or a drilling site in order to obtain "on-line" measurements while maintaining an adequate level of measurement precision for the analysis.

To this end, the invention relates to a device of the above-mentioned type, characterised in that the quantification means comprises: an optical measurement cell connected to the combustion means in order to receive the gaseous flow from the combustion means; a means for introducing a laser incident optical signal into the cell; a means for measuring a transmitted optical signal resulting from an interaction between the optical signal and each gaseous residue in the cell; and a means for calculating said content on the basis of the transmitted optical signal.

The device according to the invention may comprise one or more of the following features, taken in isolation or according to all technically possible combinations. The quantification means can comprise means for emitting an optical signal, and means for optically transmitting this signal to the introduction means, and the emission means can comprise means for adjusting the wavelength of the emitted signal, which means are able to scan a specific wavelength range for a predetermined period of time. The measurement cell can comprise: at least two mirrors which delimit a measurement cavity; means for transporting the gaseous flow to the measurement cavity; and the introduction means can comprise means for injecting the incident optical signal into the measurement cavity. At least a first mirror can have a reflectivity of less than 100%, the measurement means being arranged at the rear of the first mirror outside of the measurement cavity. The mirrors can be arranged opposite to each other along a cavity axis. The mirrors can have reflective surfaces which are arranged along the same cavity axis, with the device further comprising means for generating a plurality of reflections of the optical signal in at least two separate points on each mirror during its travel in the cavity in order to create at least two separate optical signal segments in the measurement cavity. The means for generating a plurality of reflections can comprise means for inclining the injection means in order to incline the incident optical signal to be introduced into the measurement cavity relative to the cavity axis. The separation means can comprise a gas-phase chromatograph.

The invention further relates to an assembly for analyzing at least one gaseous constituent contained in a petroleum fluid. The assembly comprises: a means for sampling the petroleum fluid; a means for extracting a gaseous sample from the fluid, which means are connected to the sampling means; and a device as defined above, with the extraction means being connected to the formation means.

The invention also relates to a method for quantifying the content of at least one gaseous constituent contained in a sample from a petroleum fluid, in which the method comprises the following steps:

formation of a gaseous flow from the sample, comprising a separation phase by means of selective retention of each gaseous constituent to be analysed;

combustion of the gaseous flow from the separation phase in order to successively form a gaseous residue from the or each constituent; and quantification of the content of the or each constituent to be analysed in the gaseous flow. The quantification step comprises the following phases: introduction of the gaseous flow from the combustion step into an optical measurement cell. For each residue successively introduced into the measurement cell:

introduction of an incident optical signal into the cell;

measurement of a transmitted optical signal resulting from an interaction between the optical signal and the or each gaseous residue in the cell; and calculation of the content on the basis of the transmitted optical signal.

The method according to the invention may comprise one or more of the following features, taken in isolation or according to all technically possible combinations. The quantification step can comprise a phase for emitting a substantially monochromatic optical signal, and a phase for optically transmitting this signal to the measurement cell in order to introduce it into the cell. The emission phase can comprise the adjustment of the wavelength of the emitted signal, and the scanning of a specific wavelength range for a predetermined period of time.

The method can comprise a step for transporting the gaseous flow to a measurement cavity which is delimited by at least two mirrors, and the introduction step can comprise a phase for injecting the incident optical signal into the measurement cavity. The mirrors can be arranged opposite to each other. At least a first mirror can have a reflectivity of less than 100%, the measurement step being carried out at a point at the rear of the first mirror outside of the cavity. The mirrors can have reflective surfaces which are arranged coaxially on a cavity axis, with the method comprising a step for generating a plurality of reflections of the optical signal in at least two separate points on each mirror during its travel in the cavity in order to create at least two separate optical signal segments in the measurement cavity. The step for generating a plurality of reflections can comprise the inclination of the incident optical signal introduced into the measurement cavity relative to the cavity axis.

BRIEF DESCRIPTION OF THE DRAWINGS

The invention will be better understood from a reading of the following description, given purely by way of example and with reference to the appended drawings, in which.

DETAILED DESCRIPTION OF THE INVENTION

A quantification device according to the invention is, for example, used in an analysis assembly 9 used for the on-line analysis of the gaseous content of drilling muds in a drilling installation 11 for drilling an oil production well.

Figure 1:
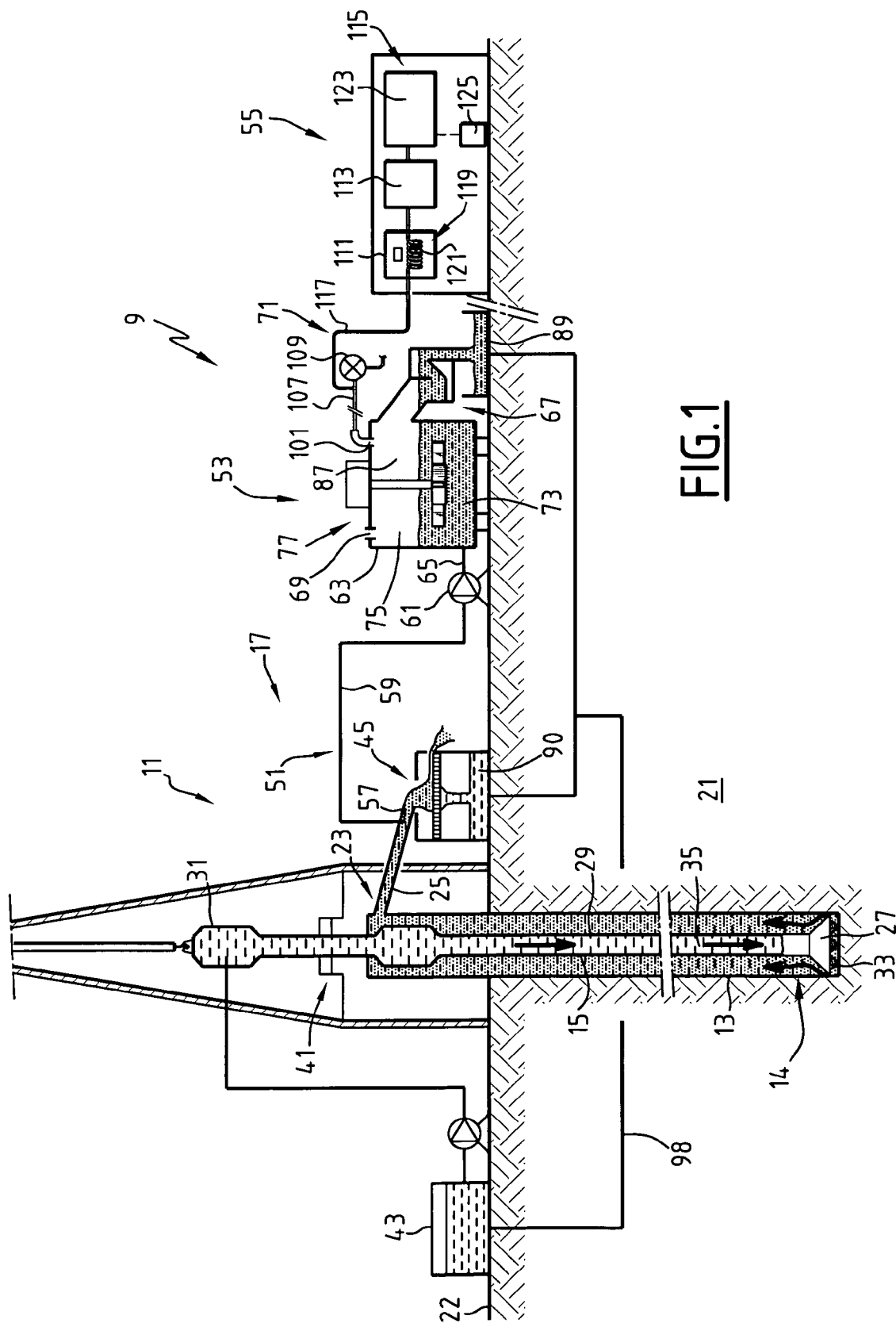
FIG. 1 is a schematic sectioned view of an analysis assembly according to the invention, arranged in an installation for drilling an oil well.

As illustrated in FIG. 1, this drilling installation 11 comprises a drilling pipe 13 in a cavity 14 through which a rotating drilling tool 15 extends, and a surface installation 17. The drilling pipe comprises, in the region of the surface 22, a well head 23 provided with a pipe 25 for discharging a drilling fluid, referred to as drilling mud. The drilling tool 15 comprises a drilling head 27, a drilling assembly 29 and a liquid injection head 31. The drilling head 27 comprises a member 33 for drilling through the rocks of the sub-stratum 21. It is assembled in the lower portion of the drilling assembly 29 and is positioned at the bottom of the drilling pipe 13. The drilling assembly 29 comprises an assembly of hollow drilling tubes. These tubes delimit an internal space 35 which allows a liquid to be conveyed from the surface 22 to the drilling head 27. To this end, the liquid injection head 31 is screwed onto the upper portion of the assembly 29.

A surface installation 17 comprises a driving unit 41 for supporting and driving the drilling tool 15 in rotation, injection unit 43 for injecting drilling liquid, and a vibrating sieve 45. The injection unit 43 is hydraulically connected to the injection head 31 in order to introduce and circulate a liquid in the inner space 35 of the drilling assembly 29. The vibrating sieve 45 collects the liquid charged with drilling residues which is discharged from the discharge pipe 25 and separates the liquid from the solid drilling residues.

As further illustrated in FIG. 1, the analysis assembly 9 comprises a sampling unit 51 for sampling the mud, and the sampling unit is tapped into the discharge pipe 25, a gas extraction device 53, and an analysis device 55 for analyzing and quantifying the extracted gases. The sampling unit 51 comprises a liquid sampling head 57 which is tapped into the discharge pipe 25, a connection tube 59, and a peristaltic pump 61 whose flow rate can be adjusted.

The extraction device 53 comprises a vessel 63, a pipe 65 for conveying the mud into the vessel 63, a discharge pipe 67 for discharging the mud from the vessel 63, an inlet 69 for introducing a carrier gas into the vessel 63, and a pipe 71 for removing the extracted gases from the vessel 63. The vessel 63 is formed by a sealed receptacle whose inner volume is, for example, between 0.4 and 3 liters. This vessel 63 comprises a lower portion 73 in which the mud circulates and an upper portion 75 which has a gaseous cap. The vessel 63 is further provided with an agitator 77 which is immersed in the mud. The mud supply pipe 65 extends between the outlet of the peristaltic pump 61 and an inlet opening which is arranged in the lower portion 73 of the vessel 63. This supply pipe 65 may be provided with a heating element for heating the mud (not illustrated) in order to bring the temperature of this mud to values of between 25 and 120° C., preferably between 60 and 90° C.

The discharge pipe 67 extends between an overflow passage 87 which is arranged in the upper portion 75 of the vessel 63 and a retaining vessel 89 which is intended to receive the mud which is discharged from the extraction device 53. It comprises a siphon in order to prevent gas from being introduced into the upper portion 75 of the vessel 63 via the discharge pipe 67. Gas is therefore introduced into the vessel 63 only via the carrier gas introduction inlet 69. The mud which is collected in the retaining vessel 89 is recycled towards the injection unit 43 via a mud recirculation pipe 98. The gas extraction pipe 71 extends between an extraction opening 101, which is arranged in the upper portion 75 of the vessel 63, and the analysis device 55. It comprises a transport line 107 which is provided with a volume flow control unit and suction means 109.

The transport line 107 connects the vessel 63 which is arranged in the vicinity of the well head 23, in the explosive zone, to the analysis device 55 which is arranged spaced apart from the well head 23 in a non-explosive zone, for example, in a pressurized cabin. This transport line 107 can be produced from a polymer material, known to be inert versus hydrocarbons, such as PTFE or THV, and has, for example, a length of from 10 m to 500 m. The suction device 109 comprises a vacuum pump which allows the gases extracted from the vessel 63 to be conveyed, by means of suction, to the analysis device 55.

Figure 2:
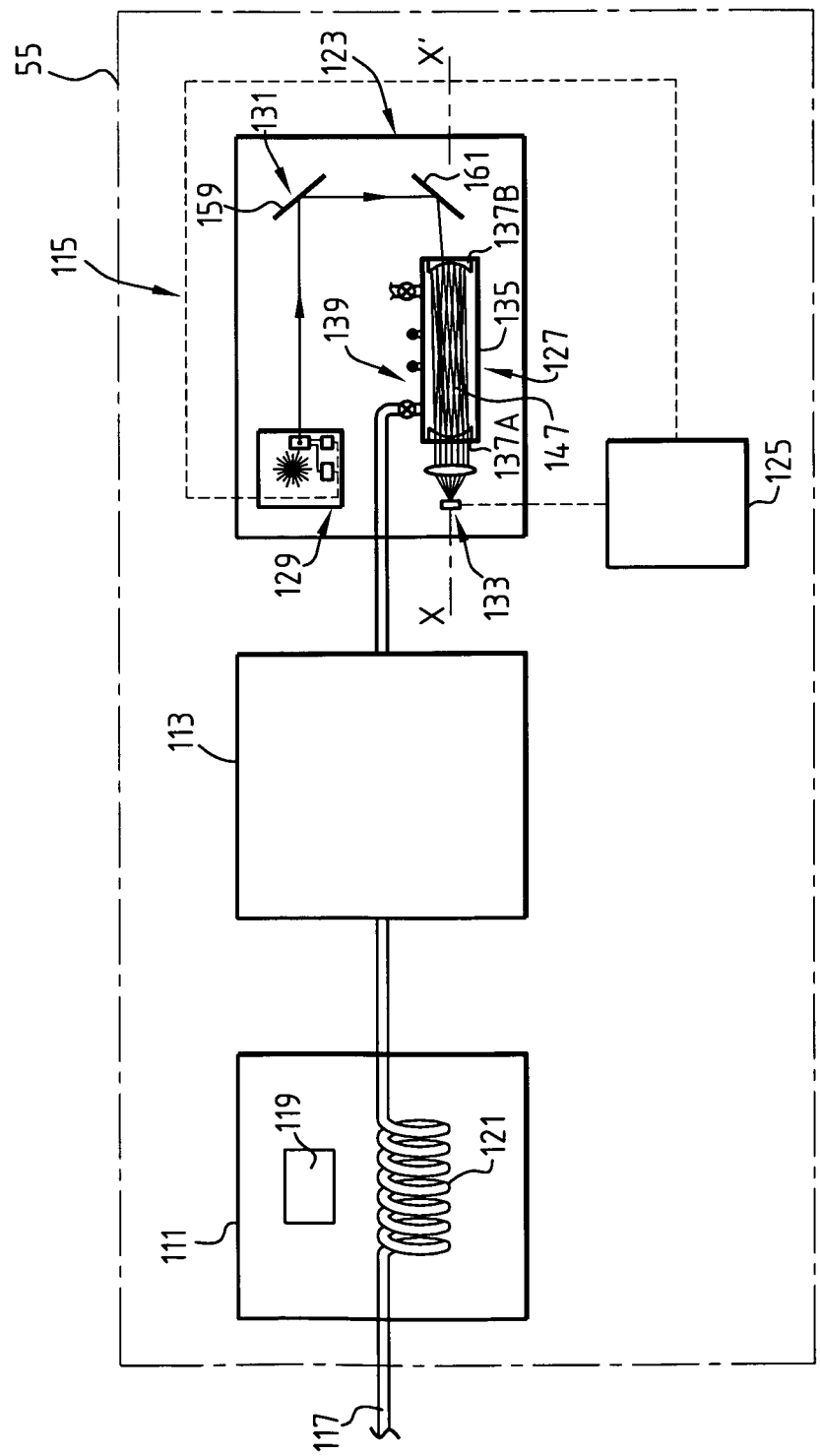
FIG. 2 is a detailed view of a first quantification device according to the invention in the analysis assembly of FIG. 1.

As illustrated in FIG. 2, the analysis device 55 according to the invention comprises a formation unit 111 for forming a gaseous flow to be analyzed, a combustion oven 113 which is connected to an outlet of the formation stage 111, and a quantification unit 115 for quantifying the content of the gaseous constituents to be analyzed in the drilling mud. The formation unit 111 comprises a sampling pipe 117 which is tapped into the extraction pipe 71 in the vicinity of the pump 109, upstream of this pump, and a gas-phase chromatograph 119 which is provided with a column 121 for separation by selective retention of the gaseous constituents to be analyzed. The chromatograph 119 is, for example, a device of the type known by those skilled in the art with a gas injection system and a chromatographic separation column 121 to separate compounds to be analyzed before their combustion in the oven 113.

The separation column 121 has a length which is between 2 m and 25 m in order to ensure a mean passage time for the gases of between 30 s and 600 s. It is connected to the sampling pipe 117 in order to take a gaseous sample from the extraction pipe 71 and form a gaseous flow at the outlet of the column 121, in which flow the sample constituents to be analyzed are separated over time.

The oven 113 comprises combustion unit for the gaseous flow discharged from the column 121 at a temperature of substantially between 900° C. and 1100° C. In the combustion unit, each constituent contained in the gaseous flow undergoes an oxidation in which the constituent reacts with oxygen to form carbon dioxide. The quantification unit 115 comprises an optical measurement unit 123 which is connected to an outlet of the combustion oven 113, and a control and calculation unit 125 which is connected electrically to the optical measurement unit 123.

Figure 3:
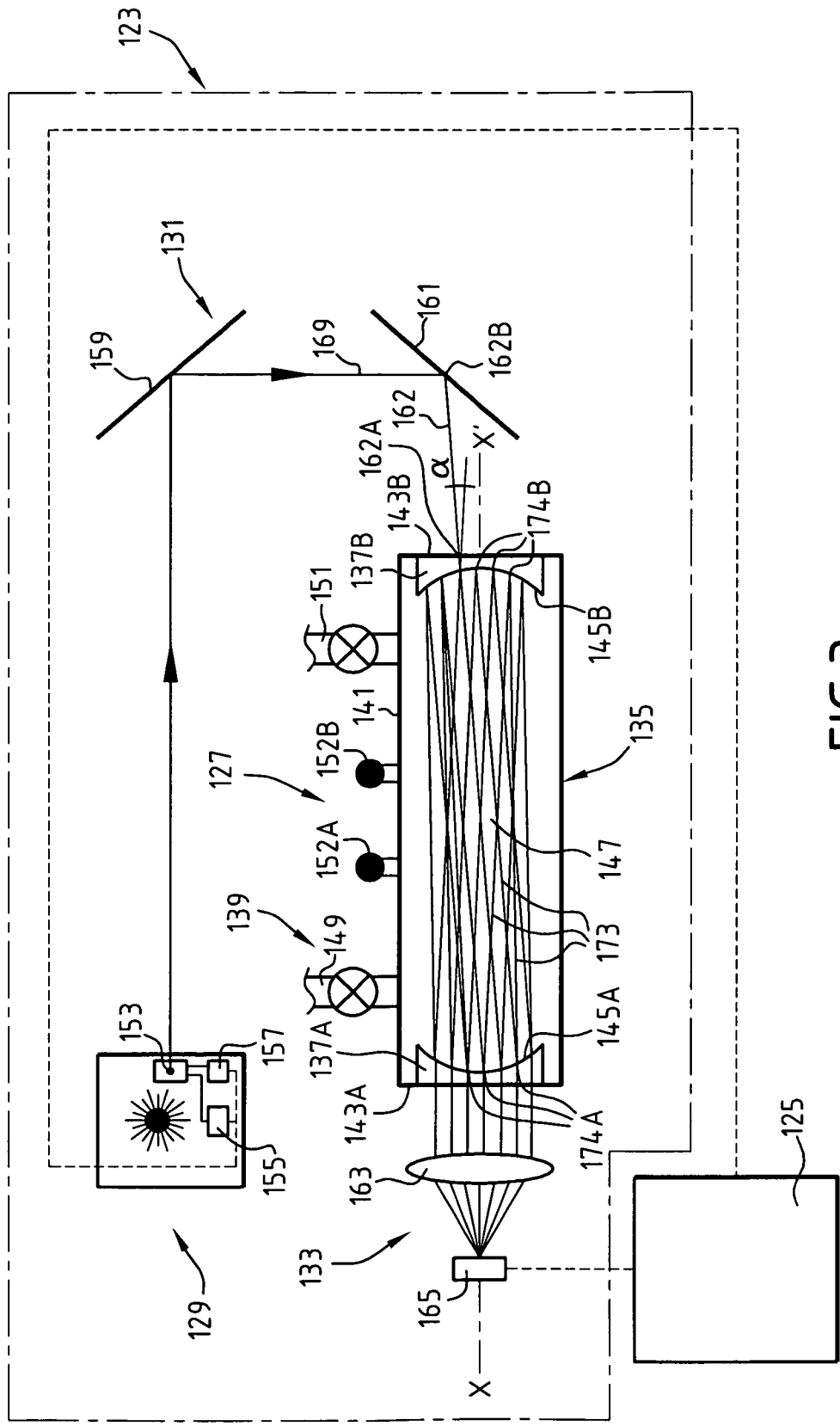
FIG. 3 is a partially sectioned schematic view of the optical measurement means of the device of FIG. 2 comprising a laser and a sensor.

As illustrated in FIGS. 2 and 3, the optical measurement unit 123 comprises an optical measurement cell 127, a laser 129 for emitting an incident optical signal, a guide mechanism 131 for introducing the incident optical signal into the optical measurement cell 127, and a sensor 133 for measuring an optical signal transmitted from the cell 127. The measurement cell 127 comprises a confinement chamber 135, two concave mirrors 137A, 137B which are fixed in the chamber 135 and a transportation unit 139 for transporting the gaseous flow from the combustion oven in the chamber 135.

With reference to FIG. 3, the chamber 135 comprises a cylindrical wall 141 which extends substantially along a longitudinal center axis X-X', and two planar end walls 143A, 143B which longitudinally close the cylindrical wall 141. The end walls 143A, 143B are transparent with respect to wavelengths in the near infrared region such as 1100 nm, 1600 nm or 2100 nm region. Each mirror 137A, 137B is fixed in the chamber 135 to a corresponding end wall 143A, 143B. The mirrors 137A, 137B are fixed coaxially along the axis X-X'. Each mirror 137A, 137B has a substantially spherical, concave reflective surface 145A, 145B which is directed towards the inner side of the chamber 135. The radius of curvature of the concave surfaces 145A, 145B is, for example, between 4 m and 8 m. The reflectivity of the mirrors 135A, 137B is greater than 50% and preferably greater than 99% for wavelengths in the near infrared regions as specified above. The concave surfaces 145A, 145B extend opposite each other symmetrically relative to a vertical center plane of the chamber 135. Together they delimit, in the chamber 135, an absorption measurement cavity (optical cavity) 147 for the interaction between the optical signal and the constituents which are introduced into the cavity 147 by the transportation unit 139. The distance which separates the surfaces 145A, 145B is substantially between 50 cm and 90 cm.

The transportation unit 139 comprises a supply pipe 149 for introducing the gaseous flow into the chamber and a discharge pipe 151. Each pipe 149, 151 is provided with a flow rate control valve 149A, 151A. The supply pipe 149 is connected to an outlet of the combustion oven 133. It opens into the chamber 135 through the wall 141, in the vicinity of the upstream mirror 137A. The discharge pipe 151 also opens into the chamber 135 in the vicinity of the downstream mirror 137. The chamber 135 is also provided with respective temperature and pressure control means 152A, 152B.

The laser 129 comprises a cavity 153 for emitting a light ray which forms a substantially monochromatic optical signal, wavelength adjustment device 155 for adjusting the mean wavelength of the signal, and intensity controller 157 for controlling the intensity of the signal. A substantially monochromatic signal is understood to be a signal which has a width at mid-range of, for example, between 0.05 nm and 1 nm. The intensity controller 157 for controlling the intensity can generate a signal having substantially constant intensity for a variable period of time.

The guide mechanism 131 comprises a deflection mirror 159 which is arranged substantially opposite the emission cavity 153, and an adjustment mirror 161 for adjusting the angle of injection into the measurement cavity 147. The adjustment mirror 161 is arranged opposite the downstream mirror 143B at the outer side of the chamber 135, and is arranged opposite the deflection mirror 159. The adjustment mirror 161 is provided with a mechanism for adjusting the injection angle α formed by the longitudinal axis X-X' and the axis of the segment 162 of the incident optical signal introduced into the cavity 147, taken between the reflection point 162B thereof on the mirror 161 and the introduction point 162A thereof in the chamber 135. The adjustment mirror 161 is further provided with means for transverse displacement relative to the axis X-X' in order to position the introduction point 162A with spacing from the axis X-X'.

The sensor 133 for measuring the transmitted optical signal comprises a focussing lens 163 which extends perpendicularly relative to the axis X-X' at the rear of the upstream mirror 137A at the outer side of the chamber 135, and an intensity detector 165 which is arranged at the focal point of the lens 163 located on the axis X-X' opposite the chamber 135 relative to the lens 163. The detector 165 is electrically connected to the control and calculation unit 125.

A first method for quantifying a constituent which is contained in a gaseous sample taken from a drilling mud and which is carried out on-line when a well is drilled will now be described with reference to FIG. 1.

In order to carry out the drilling operation, the drilling tool 15 is driven in rotation by the driving unit 41. A drilling liquid is introduced into the inner space 35 of the drilling assembly 29 by the injection means 43. This liquid moves downwards as far as the drilling head 27 and passes into the drilling pipe 13 through the drilling head 27. This liquid cools and lubricates the drilling member 33. Then the liquid collects the solid debris resulting from the drilling operation and moves upwards again through the annular space which is defined between the drilling assembly 29 and the walls of the drilling pipe 13, and is then discharged via the discharge pipe 25.

The peristaltic pump 61 is then activated in order to remove, in a continuous manner, a specific fraction of the drilling mud which is circulating in the pipe 25. This fraction of mud is conveyed as far as the chamber 63 via the supply pipe 65. The agitator 77 is driven in rotation in the lower portion 73 of the chamber 63 in order to bring about the extraction of the gases contained in the mud and the mixture of the extracted gases with the carrier gas drawn through the injection inlet 69. The gaseous mixture is extracted via the extraction pipe 71, under the action of the suction produced by the vacuum pump 109. This mixture is then conveyed as far as the analysis device 55.

The gaseous mixture containing a plurality of constituents to be analysed is then injected into the chromatograph 119 through the sampling pipe 117. A gaseous flow, in which the various constituents to be analyzed in the gaseous mixture are separated over time, is then obtained at the outlet of the column 121. This gaseous flow successively comprises, for example, $C_1$ hydrocarbons, then $C_2$ hydrocarbons and other heavier compounds. The gaseous flow then enters the oven 113 where the combustion of this flow is carried out. The various constituents which are separated in the column 121 and contained in the gaseous flow are successively converted into combustion residues, by oxidation in the oven 113. If these constituents are hydrocarbons, they form residues which are constituted principally by carbon dioxide. These residues are then conveyed into the optical measurement unit 123.

In the optical measurement unit 123, the combustion residues of the various constituents are successively introduced into the chamber 135 and circulate in the optical cavity 147 between the supply pipe 149 and the discharge pipe 151.

In the method according to the invention, immediately after the first component to be analysed has entered in the optical cavity 147, the optical cavity 147 is isolated from the gaseous flow with valves 149A and 151A to perform quantification. Then the wavelength adjustment device 155 for adjusting the wavelength is controlled to scan a wavelength range in the near infrared regions such as 1100 nm, 1600 nm or 2100 nm region (line 172 in FIG. 4) for a predetermined period of time. A scanning operation of this type is repeated for each passage of the various constituents which are to be analyzed and which circulate successively in the optical cavity 147 after opening of valves 149A and 151A. A scanning operation of this type is repeated for each passage of the combustion residues corresponding to the various constituents which are to be analyzed and which circulate successively in the optical cavity 147.

Figure 4:
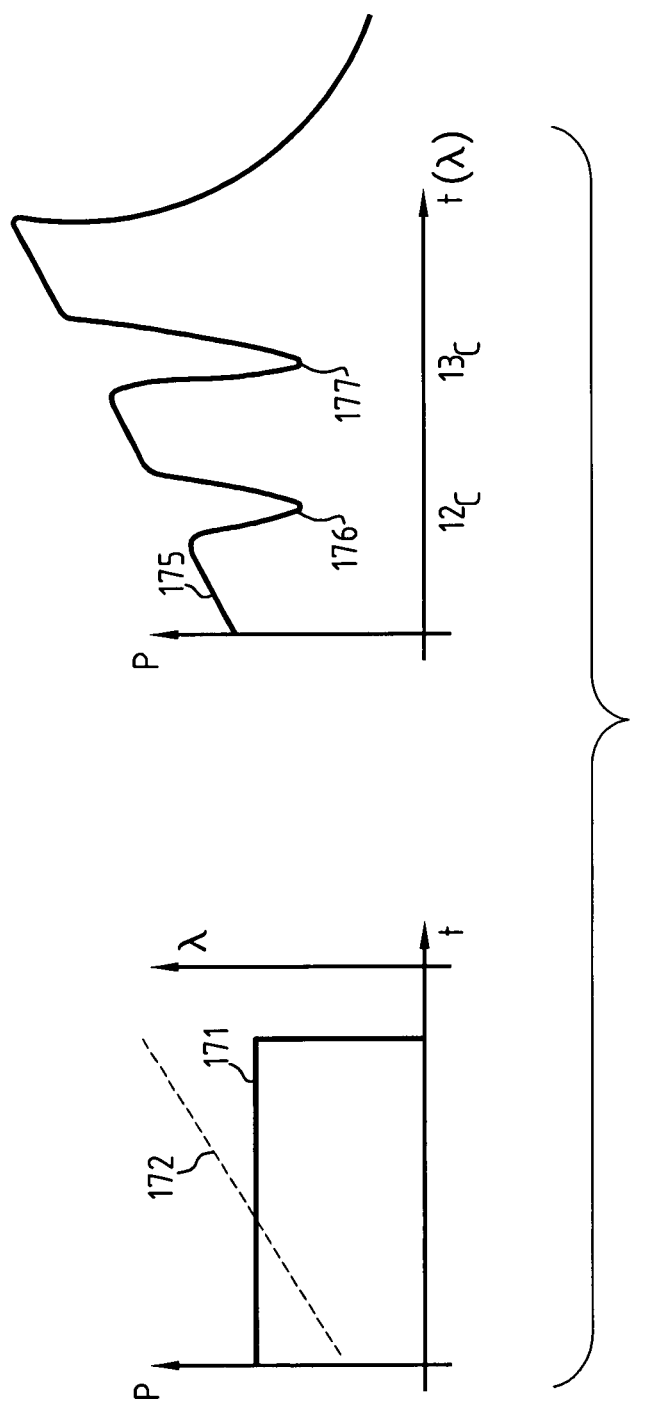
FIG. 4 is a view illustrating the emission line of the laser of FIG. 3 as a function of time, and the reception line measured by the sensor of FIG. 3 as a function of time when a method according to the invention is used.

During this scanning operation, the emission cavity 153 of the laser emits an optical signal whose intensity as a function of time is illustrated on the line 171 as a solid line in FIG. 4(*a*) and whose line 172 of the wavelength as a function of time is illustrated as a dotted line in this Figure. The incident optical signal 169 is conveyed as far as the optical cavity 147 by reflection on the deflection mirror 159 and the adjustment mirror 161, and then by transmission through the wall 143B and the mirror 137B. The incident optical signal is introduced into the cavity 147 at a point 162A which is spaced apart from the axis X-X'. The injection angle α is different from zero.

The optical signal then travels along an optical path back and forth in the optical cavity 147, formed by successive segments 173 which are delimited by a plurality of discrete reflection points 174B on each concave surface 145A, 145B. This plurality of reflections is generated by the control of the inclination of the mirror 161. The optical signal therefore covers an optical path which comprises at least 100 segments in the measurement cavity 147, and preferably at least 1000 segments.

Given the weak interactions between the various segments 173 of the optical signal formed between the successive reflection points 174A, 174B of the signal on the mirrors 137A, 137B, the optical cavity 147 has no selectivity with respect to the transmission wavelength and it is not necessary to modify the length of the cavity 147 in order to adapt to the wavelength. The optical measurement unit 123 therefore has no electronic components which are costly and difficult to use on an oil site.

The interaction of the various segments 173 and the combustion residues contained in the optical cavity 147 generates an optical signal which carries an item of information characteristic of the content of these residues in the optical cavity 147. The optical signal interacts with the molecular constituents of the measurement cell by means of vibrational excitation. The molecules absorb a portion of the optical signal resulting in a loss of optical intensity. This occurs in each segment 173 which is transmitted through the upstream mirror 137A and which is not reflected on the surface 145A.

This transmitted optical signal is focussed through the lens 163 and detected by the intensity detector 165 in order to obtain the intensity 175 as a function of time illustrated in FIG. 4(*b*). The content of combustion residues resulting from a constituent to be analyzed is, for example, calculated by the calculation unit 125 on the basis of the decay time of the intensity 175 of the transmitted signal. Furthermore, when the range of the wavelength of the incident signal is adjusted in order to scan a range in which two characteristic absorptions of two respective isotopes of the same element are produced, for example, carbon $^{12}$C and carbon $^{13}$C, the intensity 175 of the transmitted signal as a function of the wavelength shows two respective characteristic absorption regions 176 and 177 of these two isotopes. The relationship of the contents of two isotopes of the same constituent, for example, the $C_1$ hydrocarbons, in the drilling mud is then calculated on the basis of the relationship between the depths of the regions 176 and 177.

The method is then repeated during the successive passage of the residues which correspond respectively to each constituent to be analyzed in the optical cavity 147.

Figure 5:
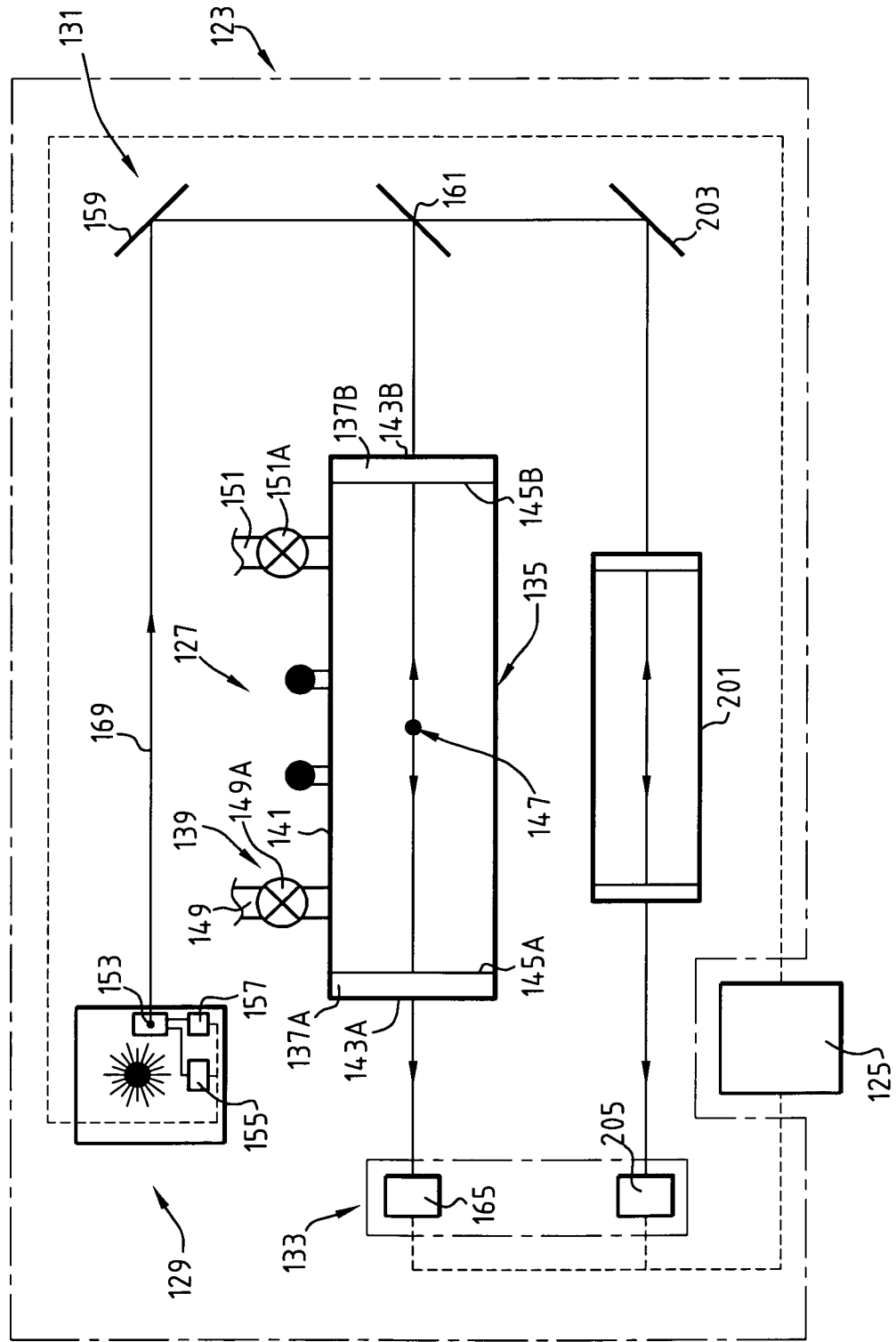
FIG. 5 is a view similar to FIG. 3 of the optical measurement means of a second quantification device according to the invention.

The second device according to the invention illustrated in FIG. 5 differs from the first device due to the structure of the optical measurement unit 123. In contrast to the unit 123 illustrated in FIG. 3, the reflective surfaces 145A, 145B of the mirrors 137A, 137B are planar. Furthermore, a second mirror in the form of an injection mirror 161 is partially reflective so that it injects only a portion of the incident optical signal into the optical cavity 147. The distance between the mirrors 137A, 137B can be adjusted in order to generate a resonance in the optical cavity 147 when a specific wavelength of the optical signal is used.

Moreover, the unit 123 further comprises a calibration cell 201 which has a similar structure to that of the optical measurement cell 127 and which is optically connected to the injection mirror 161 by a secondary deflection mirror 203 located at the rear of the injection mirror 161. The calibration cell 201 contains a compound whose content is known. A secondary detection sensor 205 is arranged opposite the cavity 201, an opposite the secondary deflection mirror 203. This sensor 205 is also connected to the control unit 125.

The operation of this second device differs from that of the first device in that a portion of the incident optical signal is reflected on the injection mirror 161 in order to be injected into the optical cavity 147 along the axis X-X', and another portion of this signal is transmitted to the secondary deflection mirror 203 through the injection mirror 161. The injection mirror 161 is arranged so that the angle of injection into the measurement cavity 147 is zero. The signal then carries out a plurality of reflections between the two intersection points between the axis X-X' and the respective reflective surfaces 145A, 145B of the mirrors 137A, 137B in the cavity 147. Furthermore, the portion of the incident optical signal which is not reflected on the injection mirror 161 is transmitted to the secondary deflection mirror 203, then injected into the secondary calibration cavity 201 along the axis Y-Y' of this cavity.

An optical calibration signal is collected by the secondary detection sensor 205 and is used as a reference by the calculation unit 125 to quantify the content of each combustion residue which circulates successively in the measurement cavity 147.

In another variant (not illustrated), the chamber has no mirrors and the incident optical signal interacts with the components contained in the cavity only along a single segment in a straight line which connects the point at which it enters the measurement cavity to the point at which it leaves the cavity.

Due to the invention which has been described above, it is possible to provide an analysis device 55 for quantifying the content of at least one gaseous constituent in a sample from a petroleum fluid, which can be readily fitted in the vicinity of a drilling installation or a well for the exploitation of fluids.

The combination of the formation unit 111 for forming a gaseous flow comprising a column 121 for separation by selective retention with a combustion oven 113 for the gaseous flow, and a quantification unit 115 for optical measurement of the content of the residues from the oven 113 allows "on-line" analysis of the gaseous compounds extracted from the fluid, while retaining a significant level of selectivity for the analysis. This selectivity in particular allows isotopic measurements to be carried out.

Furthermore, the use of an optical measurement unit 115 (quantification unit), in particular when it comprises the optical cavity 147 in which the incidence of the signal injected into the optical cavity 147 is not zero, considerably simplifies the instruments required, which allows the analysis device 55 to be readily displaced and positioned in the vicinity of a drilling installation or an oil well.

In addition, with regards to the device shown in FIGS. 2 to 4, a single laser 129 having a unique emission cavity 153 is used in the optical measurement unit 123. The range of wavelengths generated by the laser 129 when the scanning of the constituents in the optical cavity 147 is performed is wide enough to obtain two distinguishing absorptions regions corresponding to the two distinct isotopes, e.g. for carbon $^{12}C$ and carbon $^{13}C$, without the need for using two different laser sources. Moreover, the laser incident signal 169 produced in the emission cavity 153 is fully conveyed towards the optical cavity 147 without significant absorption on its path towards the optical cavity 147. The signal 169 is not split or passed through a reference cell containing a reference sample. The analysis device 55 is deprived of such a reference cell, which is not necessary for obtaining the isotopic ratios.

The invention claimed is:

1. A quantifying device for quantifying a content of at least one gaseous constituent contained in a gaseous sample from a fluid, said device comprising:
   a formation unit for forming a gaseous flow from the gaseous sample, said formation unit including a separation device for separation by selective retention of each gaseous constituent to be analyzed;
   an oven for combustion of the gaseous flow, said oven being connected to said separation device to successively form a gaseous residue from each constituent; and
   a quantification unit for quantifying the content of each constituent to be analyzed in the gaseous residue, said quantification unit including:
      an optical measurement cell including a confinement chamber for receiving the gaseous residue from said oven, and a transportation unit for transporting the gaseous residue from said oven to said confinement chamber;
      a guide mechanism for guiding a laser incident optical signal into said optical measurement cell;
      a sensor for measuring a transmitted optical signal resulting from an interaction between the laser incident optical signal introduced into said optical measurement cell and the gaseous residue received within said optical measurement cell; and
      a calculation unit for calculating the content of the gaseous residue based on the transmitted optical signal.

2. The quantifying device according to claim 1, wherein said quantification unit further includes a laser device for emitting the laser incident optical signal, said laser device including a wavelength adjustment device for adjusting a wavelength of the emitted laser incident optical signal, said wavelength adjustment device being configured to scan a specific wavelength range for a predetermined period of time;
   wherein said guide mechanism includes an introduction device for introducing the laser incident signal into said optical measurement cell, and a transmitting device for transmitting the laser incident signal to said introduction device.

3. The quantifying device according to claim 2, wherein said introduction device comprises an adjustment mirror for reflecting the laser incident optical signal toward said optical measurement cell and adjusting an angle of the laser incident optical signal relative to a longitudinal axis of said optical measurement cell, and said transmitting device comprises a deflection mirror for reflecting the laser incident optical signal toward said adjustment mirror.

4. The quantifying device according to claim 1, wherein said optical measurement cell further includes:
   at least two mirrors delimiting a confinement chamber of said optical measurement cell;
   wherein said guide mechanism includes an introduction device for introducing the laser incident signal into said confinement chamber of said optical measurement cell.

5. The quantifying device according to claim 4, wherein at least one of said at least two mirrors has a reflectivity of less than 100%, said sensor being arranged at a rear position of said at least one of said at least two mirrors and outside of said optical cavity.

6. The quantifying device according to claim 4, wherein said at least two mirrors are arranged opposite to each other along a longitudinal axis of said optical cavity.

7. The quantifying device according to claim 6, wherein said at least two mirrors have reflective surfaces arranged along said longitudinal axis of said optical cavity, wherein said introduction device is configured to generate a plurality of reflections of the laser incident optical signal in at least two separate points on each of said at least two mirrors during travel of the laser incident optical signal in said optical cavity so as to create at least two separate optical signal segments in said optical cavity.

8. The quantifying device according to claim 7, wherein said introduction device is configured to be adjustably inclined so as to incline the laser incident optical signal to be introduced into said optical cavity relative to said longitudinal axis of said optical cavity.

9. The quantifying device according to claim 1, wherein said separation device comprises a gas-phase chromatograph.

10. An assembly for analyzing at least one gaseous constituent contained in a petroleum fluid, said assembly comprising:
a sampling unit for sampling the petroleum fluid;
an extraction device for extracting a gaseous sample from the petroleum fluid, said extraction device being connected to said sampling unit; and
said quantifying device of claim 1, said extraction device being connected to said formation unit of said quantifying device.

11. A method of quantifying a content of at least one gaseous constituent contained in a gaseous sample from a fluid, said method comprising:
forming a gaseous flow from the sample, said forming comprising a separation phase by selective retention of each gaseous constituent to be analyzed;
combustion of the gaseous flow from said separation phase within an oven in order to successively form a gaseous residue from each constituent; and
quantification of the content of each constituent to be analyzed in the gaseous flow, said quantification including:
introduction of the gaseous residue formed in said combustion into a confinement chamber of an optical measurement cell by transporting the gaseous residue from the oven to the confinement chamber via a transportation unit;
introduction of a laser incident optical signal into the optical measurement cell for each gaseous residue successively introduced into the optical measurement cell;
measurement of a transmitted optical signal resulting from an interaction between the laser incident optical signal and each gaseous residue successively introduced into the optical measurement cell; and
calculation of the content of each gaseous residue successively introduced into the optical measurement cell based on the transmitted optical signal.

12. The method according to claim 11, wherein said quantification further includes emitting a substantially monochromatic laser incident optical signal, and optically transmitting the laser incident optical signal to the optical measurement cell and introducing the laser incident optical signal into the optical measurement cell, said emitting comprising adjustment of a wavelength of the emitted laser incident optical signal and scanning of a specific wavelength range for a predetermined period of time.

13. The method according to claim 11, wherein said introduction of the gaseous residue into the optical measurement cell comprises transporting the gaseous residue into an optical cavity delimited by at least two mirrors, and said introduction of the laser incident optical signal into the optical measurement cell comprises injecting the laser incident optical signal into the optical cavity.

14. The method according to claim 13, wherein the at least two mirrors are arranged opposite to each other.

15. The method according to claim 13, wherein at least a first one of the at least two mirrors has a reflectivity of less than 100%, said measurement being performed at a location at a rear of the first one of the at least two mirrors and outside of the optical cavity.

16. The method according to claim 13, wherein the at least two mirrors have reflective surfaces arranged coaxially on a longitudinal axis of the optical cavity, said introduction of the laser incident optical signal comprising generating a plurality of reflections of the laser incident optical signal in at least two separate points on each of the at least two mirrors during travel of the laser incident optical signal in the optical cavity so as to create at least two separate optical signal segments in the optical cavity.

17. The method according to claim 16, wherein said generating a plurality of reflections comprises inclining a laser incident optical signal introduced into the optical cavity relative to the a longitudinal axis of the optical cavity.

* * * * *